United States Patent
Wu et al.

[11] Patent Number: 6,075,312
[45] Date of Patent: Jun. 13, 2000

[54] MAIN STRUCTURE FOR CATCHING FLOW-INJECTION TYPE PIEZOELECTRIC SENSOR

[75] Inventors: Tzong-Zeng Wu; I-Nan Chang; Chung-Chih Lo; Wu-Chin Chan; Ray-Yi Hsu, all of Taipei, Taiwan

[73] Assignee: Smart Biotechnology Co., Ltd., Taiwan

[21] Appl. No.: 09/212,469

[22] Filed: Dec. 16, 1998

[30] Foreign Application Priority Data

| Mar. 17, 1998 | [CN] | China | 87103877 |
| Mar. 17, 1998 | [CN] | China | 87103878 |
| Jul. 30, 1998 | [CN] | China | 87212356 |

[51] Int. Cl.[7] .................................................. H01L 41/08
[52] U.S. Cl. ......................................................... 310/338
[58] Field of Search ............................... 310/328, 338, 310/339; 73/119 A, 861.61, 861.62, 861.67; 123/445, 446, 457, 458

[56] References Cited

U.S. PATENT DOCUMENTS

| 4,021,688 | 5/1977 | Kudinov et al. | 310/338 |
| 4,088,916 | 5/1978 | Weineck | 310/338 |
| 4,429,570 | 2/1984 | Tinder | 310/338 X |
| 4,432,228 | 2/1984 | Kuschmierz | 310/338 X |
| 4,556,815 | 12/1985 | Ohhashi et al. | 310/338 |
| 4,741,231 | 5/1988 | Patterson et al. | 310/338 X |

Primary Examiner—M. Budd
Attorney, Agent, or Firm—Smith, Gambrell & Russell, LLP

[57] ABSTRACT

A main structure is intended to engage and disengage an flow-injection type piezoelectric sensor and is composed of a movable stand, a lifting mechanism, and a fixed injection portion. The movable stand is capable of being actuated by a rotary shaft of the lifting mechanism to move upwards or downwards. The movable stand is provided with a retaining slot capable of catching and releasing the flow-injection type piezoelectric sensor. When the movable stand is lifted, a transparent end of the fixed injection portion is in an intimate contact with a planar surface of the flow-injection type piezoelectric sensor which is caught in the retaining slot of the movable stand. A liquid test sample is thus injected into a charge channel of the transparent end such that the liquid test sample flows on the surface of a piezoelectric crystal located in an opening of the planar surface of the flow-injection type piezoelectric sensor for detecting the presence of a target molecule in the test sample.

15 Claims, 8 Drawing Sheets

MAIN STRUCTURE FOR CATCHING FLOW-INJECTION TYPE PIEZOELECTRIC SENSOR

FIELD OF THE INVENTION

The present invention relates to a main structure for use in catching an flow-injection type piezoelectric sensor capable of engaging and disengaging a fixed injection portion of the main structure.

BACKGROUND OF THE INVENTION

This inventor of the present invention disclosed a flow-injection type piezoelectric sensor, which was allowed for issuance by the Taiwan Patent and Trademark Office and was published in THE TAIWAN PATENT GAZETTE and with the publication number of 280866. This flow-injection type piezoelectric sensor has a planar surface, a depression formed in the planar surface, and a piezoelectric crystal located in the depression such that the piezoelectric crystal is covered in two sides thereof with an upper and a lower metal electrodes. In operation, the piezoelectric crystal is contained in a biosensor device having an oscillation circuit, such that the upper and the lower metal electrodes are connected with the oscillation circuit for detecting the presence of a target molecule in a liquid sample flowing on the surface of the piezoelectric crystal. An improvement in function of the flow-injection type piezoelectric sensor described above is called for.

SUMMARY OF THE INVENTION

The primary objective of the present invention is therefore to provide an improved injection-type piezoelectric sensor with a main structure capable of engaging and disengaging the piezoelectric sensor and capable of causing the piezoelectric sensor to remain quickly in the state of being put into service.

In keeping with the principle of the present invention, the foregoing objective of the present invention is attained by a main structure of an flow-injection type piezoelectric sensor, which consists of a movable stand, a lifting mechanism located under the movable stand, and a fixed injection portion located over the movable stand.

The movable stand is provided at one end thereof with a retaining slot for engaging or disengaging the flow-injection type piezoelectric sensor. The movable stand is mounted on one or more upright pillars such that the movable stand is capable of moving up and down in a horizontal manner.

The lifting mechanism comprises a rotary shaft and a cam or protruded block fastened permanently with the rotary shaft. The rotary shaft is capable of being caught rotatably by an upright plate and capable of being rotated in one direction such that the cam or protruded block is in contact with the movable stand which is subsequently lifted by the cam or protruded block. As the rotary shaft is turned in another direction, the elevated movable stand is caused to descend in light of gravitational effect.

The fixed injection portion has one end which is transparent and provided with a charge channel and a discharge channel. The fixed injection portion further has another end which is fastened with the upright pillar or pillars. As the movable stand is lifted, the transparent end of the fixed injection portion is in an intimate contact with the planar surface of the flow-injection type piezoelectric sensor which is retained in the retaining lot of the movable stand. As a result, a liquid test sample is injected into the charge channel such that the liquid test sample flows on the surface of the piezoelectric crystal located in the depression of the planar surface. The liquid test sample is then let out via the discharge channel.

Preferably, the main structure of the present invention further comprises a spring mechanism, which is elastically confined between another end of the fixed injection portion and the movable stand. The spring mechanism consists of one or more compression springs capable of being received on the upright pillar or pillars.

Preferably, the main structure of the present invention still further comprises a handle which is fastened with one end of the rotary shaft.

Preferably, the main structure of the present invention still further comprises an O-ring, which is fastened with the fixed injection portion such that the O-ring is capable of circumventing the depression at such time when the transparent end of the fixed injection portion makes an intimate contact with the planar surface of the flow-injection type piezoelectric sensor.

Preferably, the transparent end of the fixed injection portion of the main structure of the present invention has a protuberance which is capable of being inserted into the depression without making contact with the piezoelectric crystal at the time when the transparent end of the fixed injection portion makes an intimate contact with the planar surface of the flow-injection type piezoelectric sensor.

Preferably, the charge channel and the discharge channel of the main structure of the present invention are in the cross form and in different planes. More preferably, the charge channel is provided with an inlet contiguous to the protuberance, whereas the discharge channel is provided with an outlet contiguous to the protuberance and opposite to the inlet.

The foregoing objective, features, functions, and advantages of the present invention will be more readily understood upon a thoughtful deliberation of the following detailed description of the embodiments of the present invention with reference to the accompanying drawings.

DETAILED DESCRIPTION OF THE EMBODIMENTS

As shown in FIGS. 1–4, a main structure for catching an flow-injection type piezoelectric sensor of the present invention is composed of the component parts, which are described hereinafter.

The main structure of the present invention comprises an upright plate 10 and a pair of support pillars 11 parallel to the upright plate 10, by which the main structure of the present invention is able to stand on a horizontal plane.

A movable stand 20 is movably fastened with the support pillars 11 such that the movable stand 20 is capable of a reciprocating motion on the support pillars 11. The movable stand 20 is provided therein with an oscillation circuit (not shown in the drawings). The movable stand 20 is further provided in one side thereof with a retaining slot 21 capable of catching and releasing an flow-injection type piezoelectric sensor 50.

A rotary shaft 12 is fastened in tandem with the upright plate 10 and the movable stand 20 such that a handle 13 fastened at an outer end of the rotary shaft 12 is capable of actuating the rotary shaft 12 to rotate.

A cam 14 is mounted on the rotary shaft 12 such that the cam 14 can be actuated to turn along with the rotary shaft 12.

A fixed injection portion is located on the support pillars 11 by fastening elements 41. The fixed injection portion has one end 30 which is transparent and is provided with three charge channels 32 and three discharge channels 33. The fixed injection portion further has another end 40 which is fastened securely with the support pillars 11. The charge channel 32 and the corresponding discharge channel 33 are arranged slantingly and in the cross form and in different planes to enhance occurrence of a laminar flow pattern in a recess of the flow-injection type piezoelectric sensor 50. Alternatively, the charge channel 32 and the corresponding discharge channel 33 may be arranged slantingly and in the same planes.

Two compression springs 42 are fitted over the support pillars 11 such that the two compressor springs 42 are elastically confined between the fastening end 40 and the movable stand 20.

The underside of the transparent end 30 of the fixed injection portion of the main structure of the present invention is provided with three O-rings 34 attached thereto such that each of the three O-rings 34 encircles an inlet 321 of one of the three charge channels 32 and an outlet 331 of one of the three discharge channels 33.

The flow-injection type piezoelectric sensor 50 is provided in the upper surface thereof with three openings 51 which are arranged equidistantly, and with a piezoelectric crystal located in the opening 51. When the flow-injection type piezoelectric sensor 50 is caught in the retaining slot 21, each opening 51 is aligned with the undersides of the charge channel 32 and the discharge channel 33. When the transparent end 30 is in an intimate contact with the flow-injection type piezoelectric sensor 50, the opening 51 is circumvented by the O-ring 34 and is in communication with the inlet 321 of the charge channel 32 and the outlet 331 of the discharge channel 33.

The charge channels 32 and the discharge channels 33 are provided respectively in two sides of the transparent end 30 with a connection port 31 for connecting an outside conduit for conveying a liquid test sample.

As the rotary shaft 12 and the cam 14 are actuated by the handle 13, the movable stand 20 is forced to move toward the fixed injection portion until the movable stand 20 is in contact with the fixed injection portion. The test sample is thus injected into the charge channel 32 via the connection port 31 and the inlet 321. The test sample is subsequently injected into the opening 51 of the flow-injection type piezoelectric sensor 50, before passing the piezoelectric crystal. Thereafter, the test sample is let out of the transparent end 30 via the outlet 331 and the discharge channel 33. As a result, the presence of a target molecule in the test sample can be detected. The compression springs 42 located under the fastening end 40 are compressed when the process described above is under way. Upon completion of the testing, the handle 13 is turned in reverse to cause the cam 14 to rotate in reverse so as to relieve the movable stand 20 of the pressure, thereby enabling the movable stand 20 to be pushed in reverse by the elastic force of the compressed compression springs 42. As a result, the flow-injection type piezoelectric sensor 50 becomes disengaged with the fixed injection portion. In the meantime, the flow-injection type piezoelectric sensor 50 can be removed with ease and speed from the retaining slot 21 of the movable stand 20.

Figure 1:
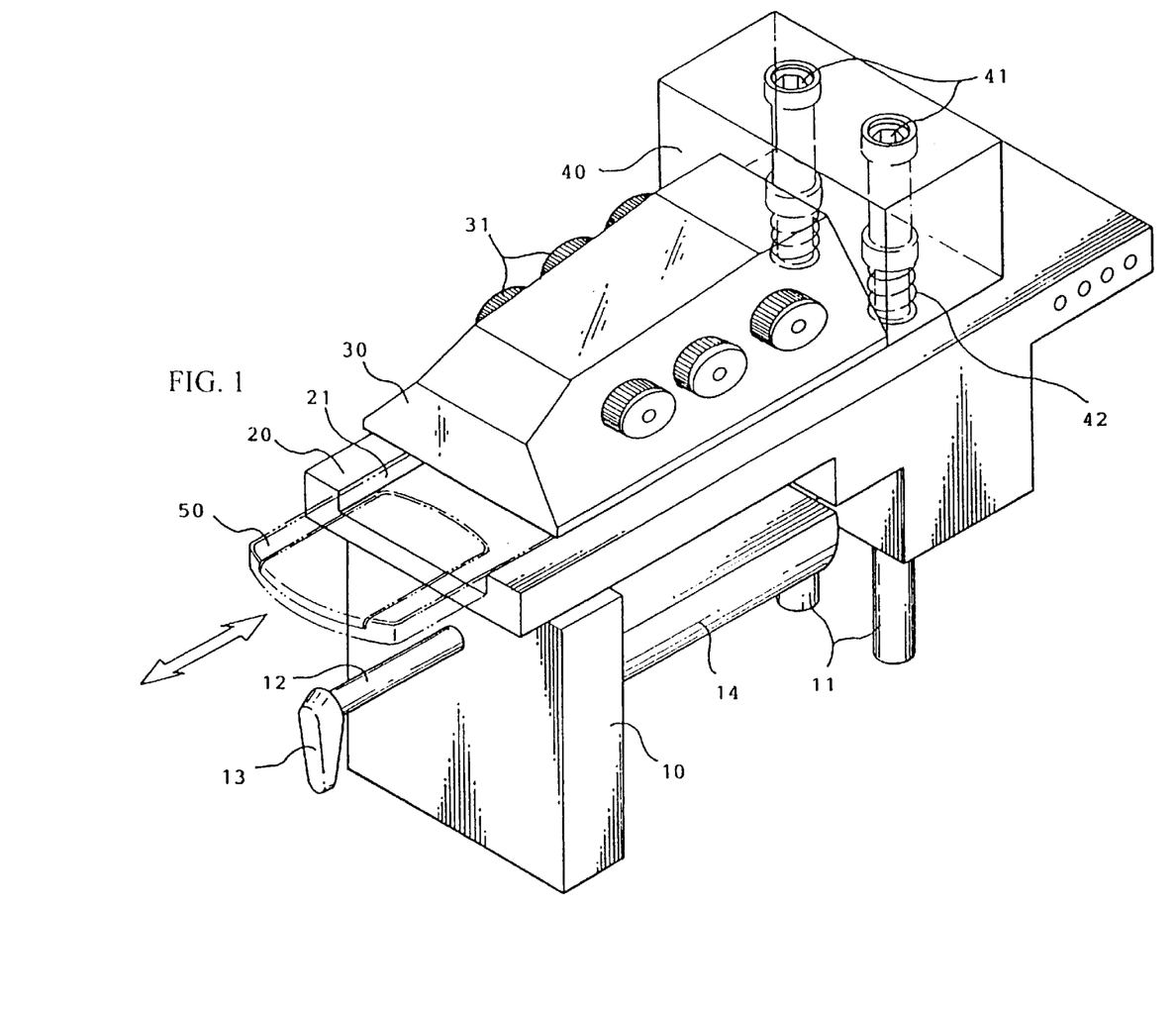
FIG. 1 shows a perspective view of a first preferred embodiment of the present invention.
Figure 2:
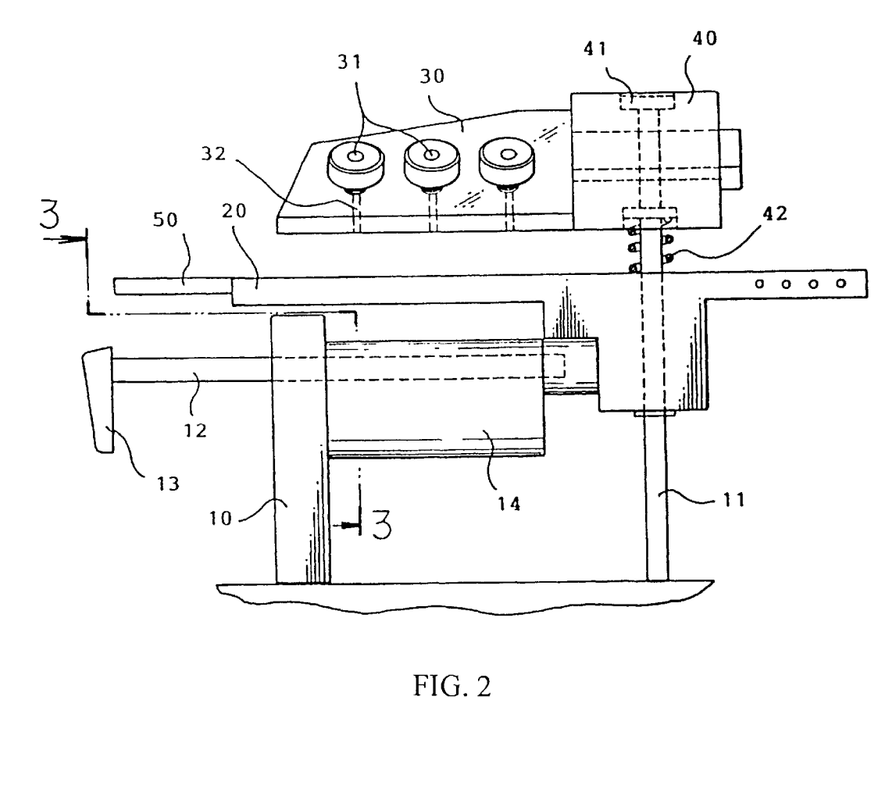
FIG. 2 shows a side view of a first preferred embodiment of the present invention.
Figure 3:
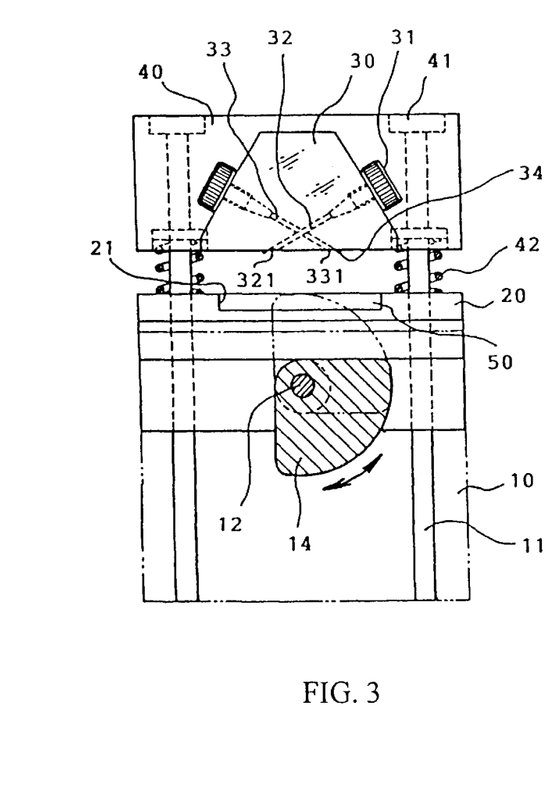
FIG. 3 shows a sectional view of a portion taken along the direction indicated by a line 3—3 as shown in FIG. 2.
Figure 4:
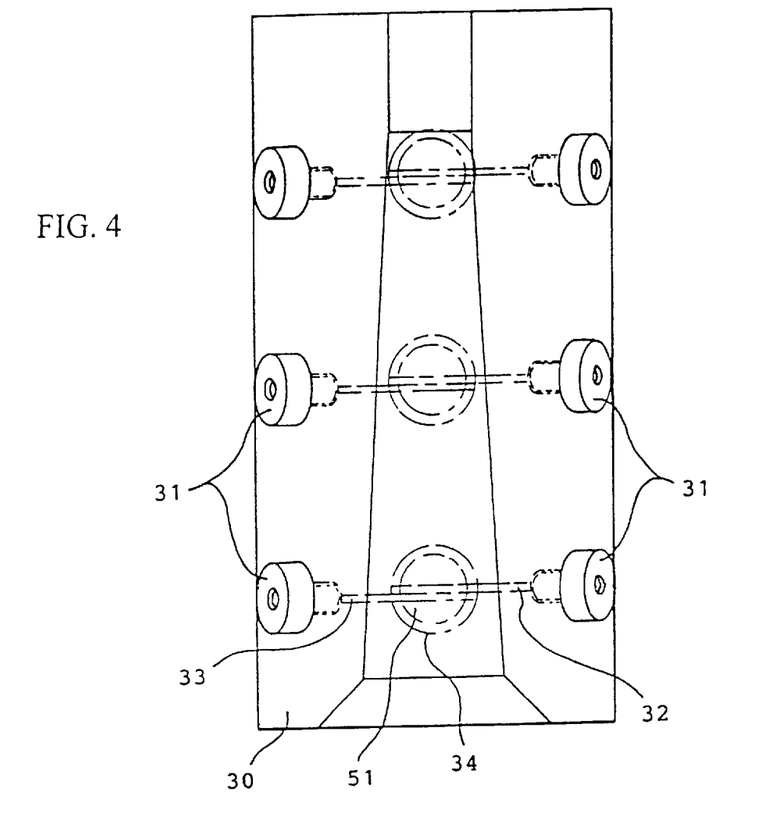
FIG. 4 shows a bottom view of the transparent end of the fixed injection portion of the first preferred embodiment of the present invention.
Figure 5:
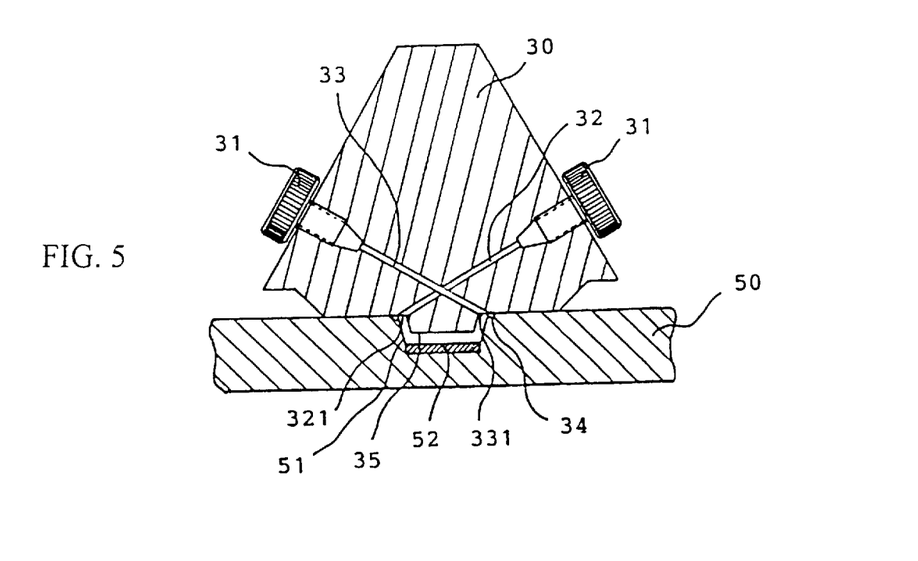
FIG. 5 shows a partial sectional view of a second preferred embodiment of the present invention.
Figure 6:
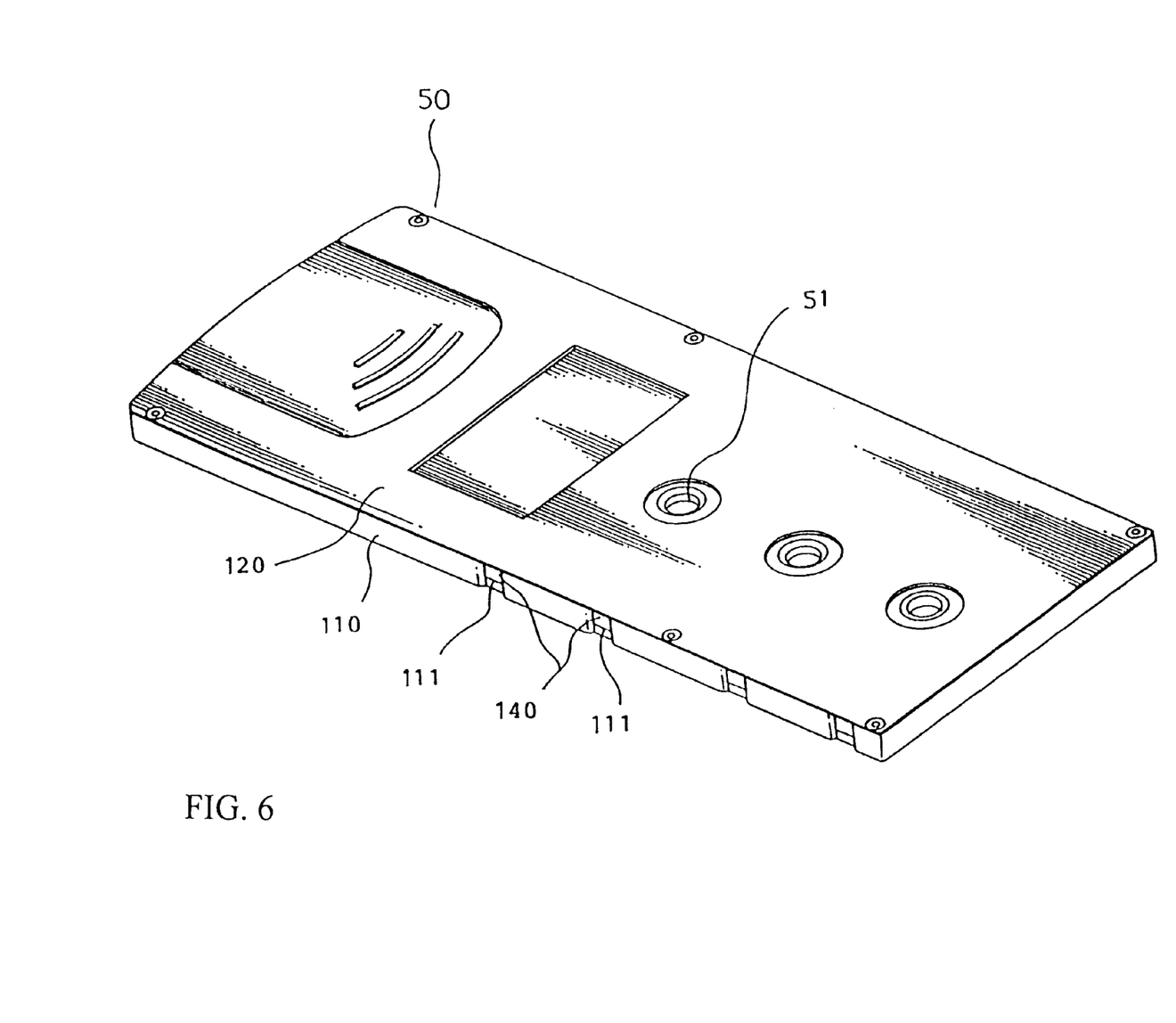
FIG. 6 shows a perspective view of an flow-injection type piezoelectric sensor suitable for use in the present invention.
Figure 7:
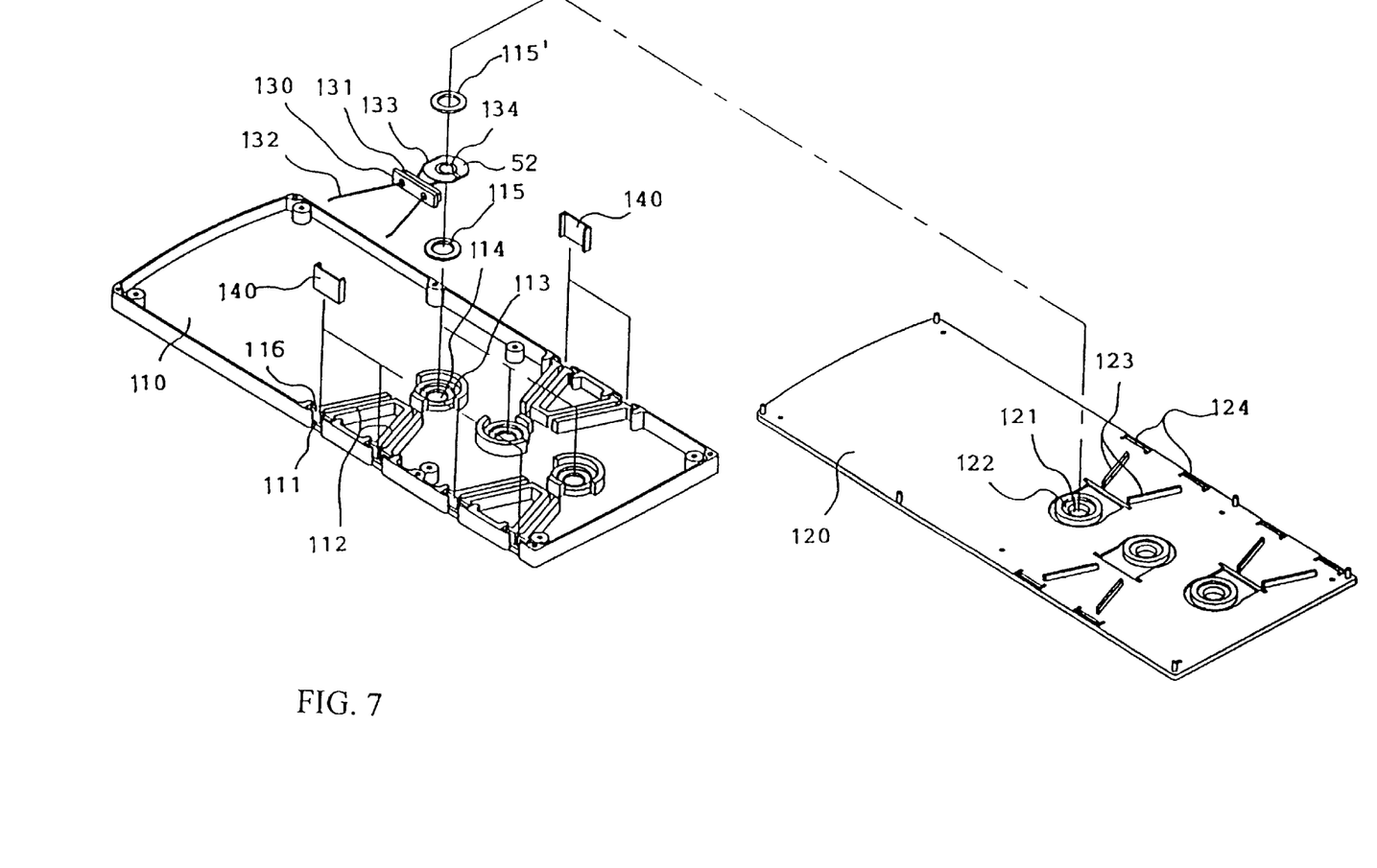
FIG. 7 shows an exploded view of the flow-injection type piezoelectric sensor as shown in FIG. 6.
Figure 8:
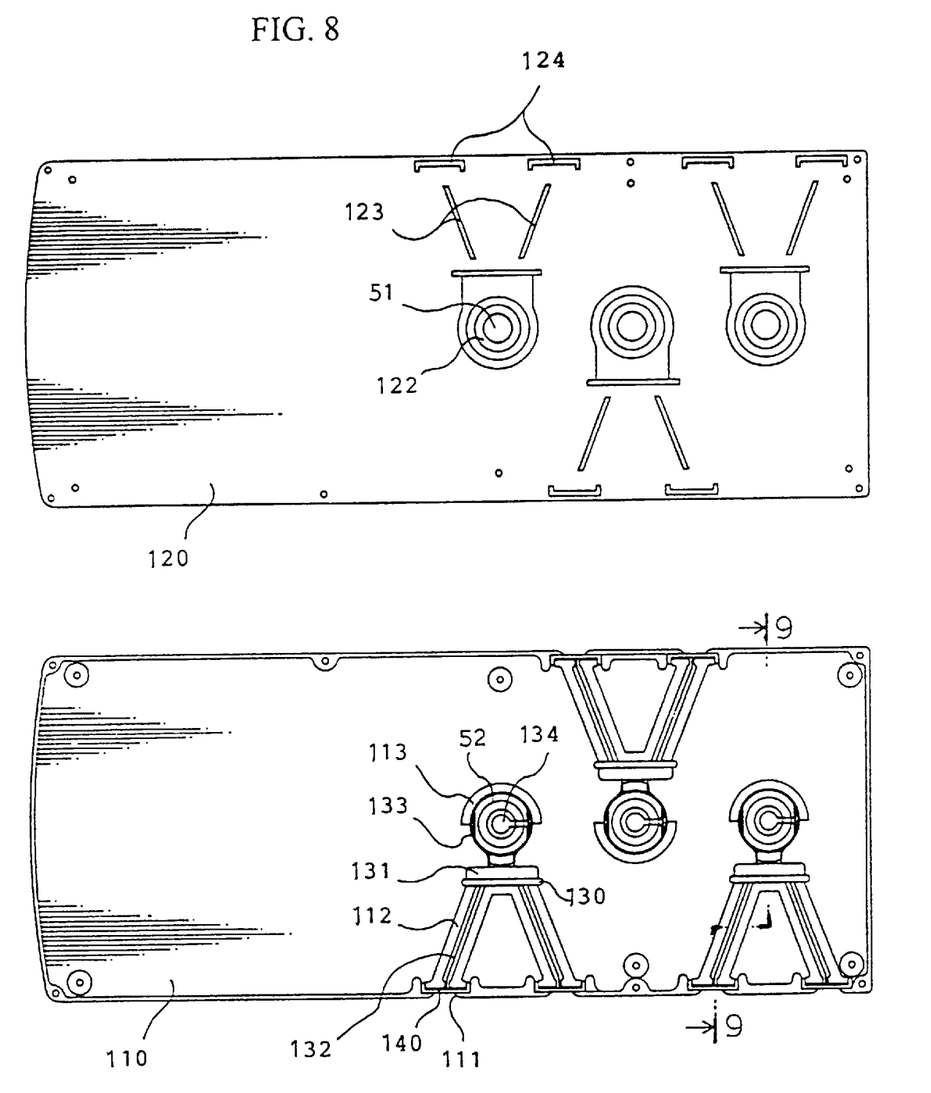
FIG. 8 shows a top plan view of the flow-injection type piezoelectric sensor as shown in FIG. 6.
Figure 9:
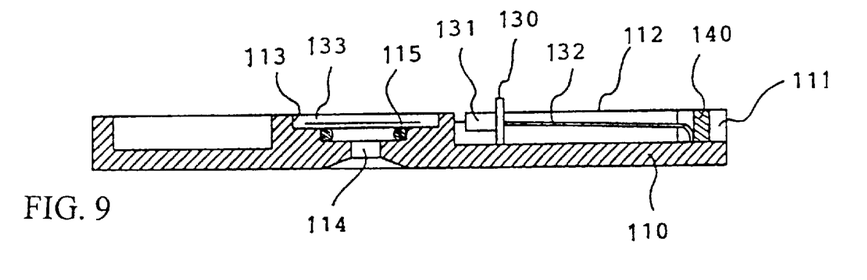
FIG. 9 shows a sectional view of a portion taken along the direction indicated by a line 9—9 as shown in FIG. 8.

As shown in FIG. 5, the second preferred embodiment of the present invention is basically similar to the first preferred embodiment described above, except that the former has three protuberances 35 located in the underside of the transparent end 30 of the fixed injection portion, and between the inlet 321 of the charge channel 32 and the outlet 331 of the discharge channel 33. When the transparent end 30 makes an intimate contact with the upper surface of the flow-injection type piezoelectric sensor 50, the protuberances 35 are inserted into the openings 51 without making contact with the piezoelectric crystal 52.

As shown in FIGS. 6–9, the piezoelectric sensor 50 used in the present invention is composed of a bottom seat 110 and a cap 120, which form together a cassette. The bottom seat 110 is provided with a plurality of clamping devices for holding the crystal, and a catch seat 113 having a through hole 114. The bottom seat 110 is provided in the periphery thereof with two indentations 111 which are corresponding in location to the catch seat 113 and capable of exposing two conductive pieces 140. The indentations 111 are provided therein with two conductive piece locating slots 116 and two terminal locating slots 112. The catch seat 113 is provided with a lower O-ring 115.

The cap 120 is similar in shape to the bottom seat 110 and is provided with a ring seat 122 having an opening 121 and corresponding in location to the catch seat 113, a rib 123 and a retaining slot 124. The cap 120 is joined with the bottom seat 110 such that the ring seat 122 is joined with the catch seat 110. The ring seat 122 is provided with an upper O-ring 115'.

A piezoelectric crystal 52 is held by a crystal clamping device 130 and is deposited with an upper metal electrode 134 on one side thereof having an area smaller than the crystal 52. The upper metal electrode 134 has a projected portion extending to reach one end of the crystal 52. The piezoelectric crystal 52, on another side thereof, is further deposited with a lower metal electrode (not shown in the drawing) corresponding in shape to the upper metal electrode 134 and having a projected portion extending to reach another end of the crystal 52.

The crystal clamping device 130 has a base seat 131 and two lead wires 133 having one end which is extended from one side of the base seat 131 to form two terminals 132, with another end extending from another side of the base seat 131 to hold both ends of the crystal 52 and to connect the projected portions of the upper metal electrode 134 and the lower metal electrode. The crystal clamping device 130 is disposed in the bottom seat 110 such that the crystal 52 is caught in the catch seat 113 and on the O-ring 115, and that the terminals 132 are caught in the terminal locating slots 112.

The conductive piece 140 is made of a metal material conductive to electricity and is inserted into the conductive piece locating slot 116 of the bottom seat 110 such that the conductive piece 140 is in contact with the terminal 132 of the crystal clamping device 130. The cap 120 is secured to the bottom seat 110 by means of screws (not shown in the drawings) or high-frequency melting. The crystal 52 and the upper metal electrode 134 are exposed through the openings 51 of the ring seat 22. The terminal 132 of the clamping device is in contact with the conductive piece 111 located in the locating slot 116. The flow-injection type piezoelectric sensor 50 is engaged with the main structure of the present invention such that the conductive piece 111 is in contact with the oscillation circuit of the main structure for detecting the presence of a target molecule in the liquid test sample by flowing the test sample on the surface of the piezoelectric crystal 52 and the upper metal electrode 134.

It is therefore readily apparent that the present invention has advantages, which are described hereinafter.

The efficiency of testing the sample is greatly enhanced by the present invention in view of the fact that the flow-injection type piezoelectric sensor 50 can be easily engaged and disengaged with the main structure of the present invention.

The present invention prevents the formation of air bubbles in light of an intimate contact between the piezoelectric crystal 52 and the charge channel 32 and the discharge channel 33 of the fixed injection portion.

The present invention enhances the reliability of the test result in light of the protuberances 35 enabling the liquid test sample to flow on the surface of the piezoelectric crystal 52 in a laminar flow pattern.

Figure 10:
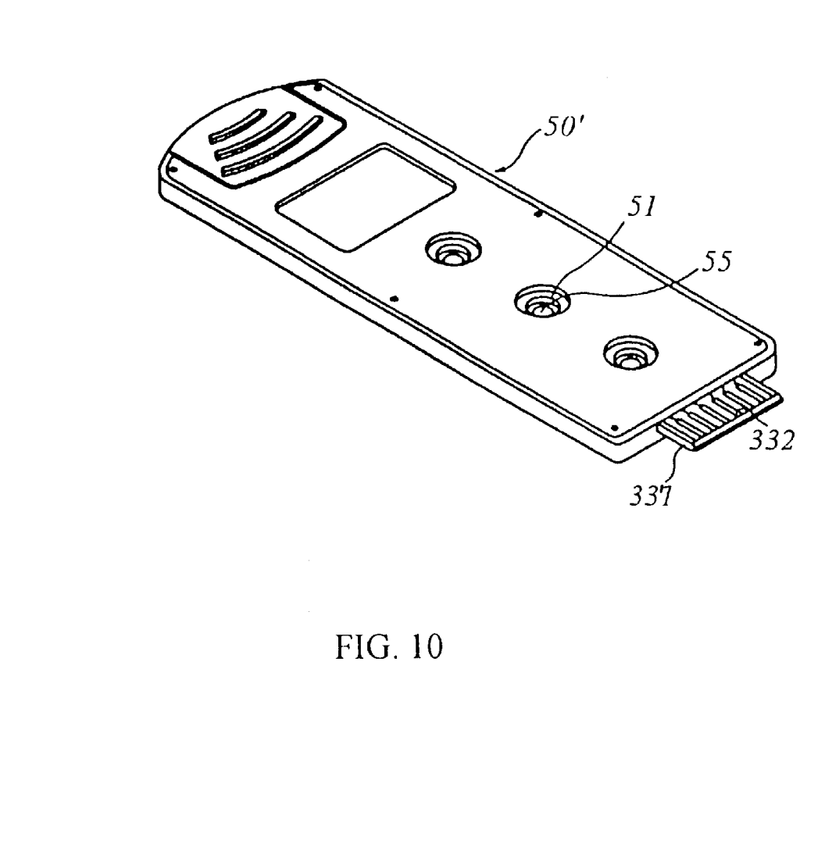
FIG. 10 shows a perspective view of another flow-injection type piezoelectric sensor having a plug-in card suitable for use in the present invention.

Another flow-injection type piezoelectric sensor 50' having a plug-in card for use in the present invention is shown FIG. 10. The piezoelectric sensor 50' is provided in the upper surface thereof with three openings 51 which are arranged equidistantly, and a gold-finger plug-in card 337. Each of the openings is provided therein with a piezoelectric crystal unit 55, and the gold-finger plug-in card 337 is provided on the upper and lower surfaces with six printed conductive lines 332 respectively.

When the flow-injection type piezoelectric sensor 50' is caught in the retaining slot 21 of the main structure, each opening 51 is aligned with the undersides of the charge channel 32 and the discharge channel 33. When the transparent end 30 is in an intimate contact with the flow-injection type piezoelectric sensor 50', the opening 51 is circumvented by the O-ring 34 and is in communication with the inlet 321 of the charge channel 32 and the outlet 331 of the discharge channel 33. Moreover, the gold-finger plug-in card 337 of the piezoelectric sensor 50' is in contact with the oscillation circuit of the main structure for detecting the presence of a target molecule in the liquid test sample by flowing the test sample on the piezoelectric crystal unit 55 through the openings 51 of the piezoelectric sensor 50'.

Figure 11:
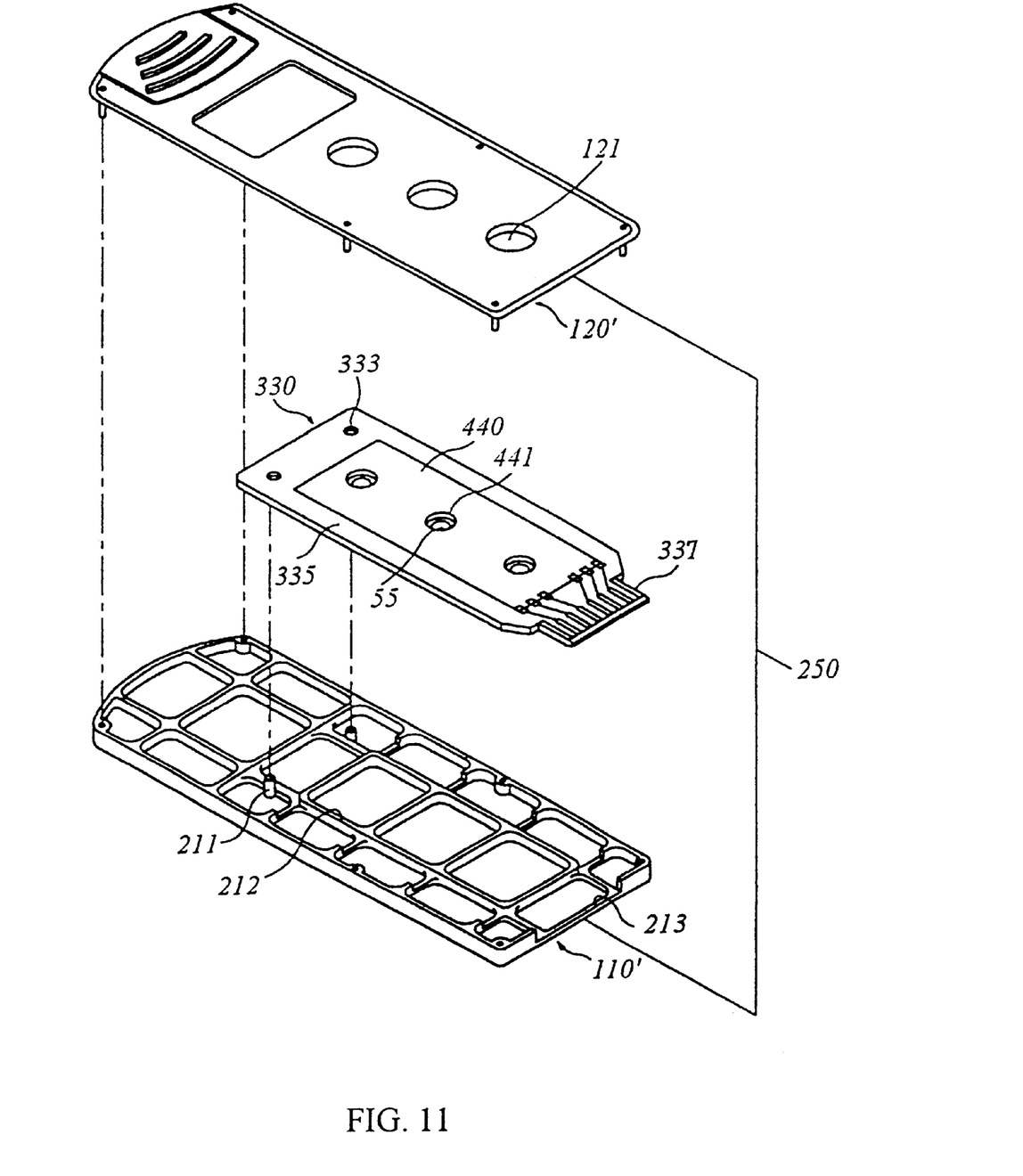
FIG. 11 shows an exploded view of the flow-injection type piezoelectric sensor as shown in FIG. 10.

As shown in FIGS. 10 and 11, the piezoelectric sensor 50' contains a cassette 250 and a printed circuit board 330. The cassette 250 is composed of a cap 120' and a bottom seat 110', wherein two pillars 211 and an upright grid 212 are provided in the bottom seat 110' for connecting with holes 330 provided in the printed circuit board 330 and for supporting the printed circuit board 330, respectively. The bottom seat 110' further has an indentation 213 to accommodate the plug-in card 337 of the printed circuit board 330.

The printed circuit board 330 basically is composed of a surrounding frame 335 and a central panel 440. The central panel 440 has three apertures 441 equidistantly spaced apart with one another, each of which is sealed with the piezoelectric crystal unit 55 at the bottom thereof. The central panel 440 is made of ceramic material and has smooth surfaces.

The cap 120' has a shape and size corresponding to those of the bottom seat 110', and is secured to the bottom seat 110' by means of screws (not shown in the drawings) or high-frequency melting to seal the printed circuit board 330 therein with the plug-in card 337 protruding from the cassette 250. The cap 120' further has three openings 121 corresponding to the apertures 441 so that the piezoelectric crystal units 55 will be exposed from the openings 51 of the cassette 250 as shown in FIG. 10.

The printed circuit board 330 shown in FIG. 11 will be described in details by referring to FIG. 12, in which the printed circuit board 330 is rotated by 180°. The surrounding frame 335 is similar to a conventional printed circuit board and has a detaining hole 336 having a size and shape corresponding to those of the central panel 440. However, the detaining hole 336 is not uniform in size, and it has a greater opening at the lower portion and the size is gradually reduced towards the upper portion. The size of the central panel 440 is between the larger opening and the smaller opening of the detaining hole 336, so that the central panel 440 is able to be received by the detaining hole 336 from the bottom and hold between the bottom surface and top surface of the surrounding frame 336. Preferably, the bottom surface of the central panel 440 and the bottom surface of the surrounding frame 336 are co-planar, after the central panel 440 is retained by the surrounding frame 336. Six printed conductive lines 449 on the central panel 440 are separately adjacent to six soldering pads 339 provided on the surrounding frame 336, and are then soldered to the corresponding pads to electrically connected to the printed conductive lines 332 on the plug-in card 337, as shown in FIG. 11.

Figure 12:
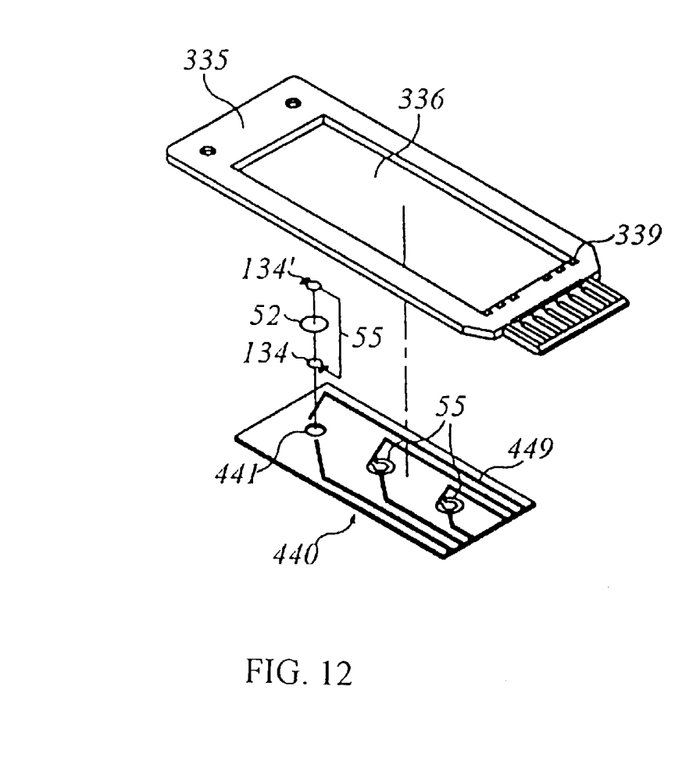
FIG. 12 shows an exploded view of a printed circuit board 330 of the flow-injection type piezoelectric sensor as shown in FIG. 11.

As shown in FIG. 12, the piezoelectric crystal unit 55 comprises a piezoelectric crystal 52, an upper metal electrode 134 and a lower metal electrode 134'. The size of the piezoelectric crystal 52 is large enough to cover the aperture 441 of the central panel 440. The upper metal electrode 134 having an area smaller than the crystal 52 is deposited on one side thereof. The upper metal electrode 134 has a projected portion extending to reach one end of the crystal 52. The piezoelectric crystal 52, on another side thereof, is further deposited with the lower metal electrode 134' corresponding in shape and size to the upper metal electrode 134 and having a projected portion extending to reach another end of the crystal 52. The piezoelectric crystal unit 55 is attached to the aperture 441 of the central panel 440 with a metallic conductive glue after the two projected portions of the metal electrodes 134, 134' being aligned with two terminals of two printed conductive lines 449 on the central panel 440. Immediately prior to the attachment, a molten solder is formed on one of the two terminals, and the projected portion of the upper metal electrode 134 is then soldered to the terminal having molten solder after the attachment. The projected portion of the lower metal electrode is finally soldered to another terminal of the two printed conductive lines 449 on the central panel 440.

The flow-injection type piezoelectric sensor 50' having a plug-in card shown in FIGS. 10–12 has a low fabrication cost and is easy to be manufactured as a result of the integrated design. Moreover, the ceramic central panel 440 is more resistant to an acidic or alkaline liquid test samples.

What is claimed is:

1. A main structure of an flow-injection type piezoelectric sensor, said flow-injection type piezoelectric sensor having a planar surface, an opening located in said planar surface, and a piezoelectric crystal located in said opening, said main structure comprising:

a movable stand provided at one end thereof with a retaining slot capable of catching and releasing the flow-injection type piezoelectric sensor, said movable stand being horizontal and movably engaged on one or more upright support pillars;

a lifting mechanism located under said movable stand and composed of a rotary shaft and a cam or protruded block fastened with said rotary shaft, said rotary shaft being rotatably mounted on an upright plate such that said rotary shaft can be rotated in one direction so as to cause said cam or protruded block to raise said movable stand, and then said rotary shaft can be rotated in another direction so as to cause said movable stand to descend in light of the gravitational effect; and a fixed injection portion located over said movable stand and provided with a transparent end having a charge channel and a discharge channel, said fixed injection portion provided with a fastening end which is fastened with said one or more support pillars such that said transparent end is capable of making an intimate contact with the planar surface of the flow-injection type piezoelectric sensor at such time when said movable stand is lifted, and that a liquid test sample is thus able to be injected into said charge channel to flow through the piezoelectric crystal before being discharged via said discharge channel.

2. The main structure as defined in claim 1 further comprising a spring mechanism confined between said fastening end of said fixed injection portion and said movable stand.

3. The main structure as defined in claim 2, wherein said spring mechanism consists of one or more compression springs mounted on said one or more support pillars.

4. The main structure as defined in claim 1 further comprising a handle fastened with one end of said rotary shaft.

5. The main structure as defined in claim 1 further comprising an O-ring which is joined with said fixed injection portion and is capable of circumventing said opening at such time when said transparent end is in an intimate contact with the planar surface of the flow-injection type piezoelectric sensor.

6. The main structure as defined in claim 1, wherein said transparent end of said fixed injection portion is provided with a protuberance capable of being inserted in said opening without making contact with the piezoelectric crystal at such time when said transparent end is in an intimate contact with the planar surface of the flow-injection type piezoelectric sensor.

7. The main structure as defined in claim 1, wherein said charge channel and said discharge channel are in the cross form and in different planes, or said charge channel and said discharge channel are in the same plane and opposite to each other.

8. The main structure as defined in claim 6, wherein said charge channel has an inlet contiguous to said protuberance; and wherein said discharge channel has an outlet contiguous to said protuberance and opposite in location to said inlet.

9. The main structure as defined in claim 8, wherein said charge channel and said discharge channel are in the cross form and in different planes.

10. The main structure as defined in claim 1 further comprising the flow-injection type piezoelectric sensor which in turn comprises:

a bottom seat and a cap joined with said bottom seat to form a cassette for containing a plurality of clamping devices each capable of holding a piezoelectric crystal, said bottom seat provided with a plurality of catch seats each having a through hole, per catch seat of said plurality of catch seats, said bottom seat further provided in a periphery thereof with two indentations, two conductive piece locating slots adjacent to said two indentations, and two terminal locating slots between said catch seat and said two conductive piece locating slots;

a plurality of first O-rings being engaged with said plurality of catch seats correspondingly;

said plurality of clamping devices each having said piezoelectric crystal, a base seat and two lead wires, said piezoelectric crystal being deposited with an upper metal electrode on one side thereof, said upper metal electrode having an area smaller than that of said piezoelectric crystal and having a projected portion extending to reach one end of said piezoelectric crystal, said piezoelectric crystal being further deposited with a lower metal electrode on another side thereof corresponding in shape to said upper metal electrode and having a projected portion extending to reach another end of said piezoelectric crystal, said two lead wires having one end which is extended from one side of said base seat to form two terminals, said two lead wires having another end which is extended from another side of said base seat to hold both ends of said piezoelectric crystal and to connect said projected portions of said upper metal electrode and said projected portions of said upper metal electrode and said lower metal electrode, said plurality of clamping devices being disposed in said bottom seat such that said piezoelectric crystals are caught in said plurality of catch seats and on said plurality of first O-rings separately, and that said two terminals of each one of said plurality of clamping devices are caught in said two terminal locating slots;

two conductive pieces made of a metal material conductive to electricity per catch seat of said plurality of catch seat, with said two conductive pieces being inserted into said two conductive piece locating slots separately such that said two conductive pieces are partially exposed through said two indentations separately, and that said two said conductive pieces are in contact with said two terminals caught in said two terminal locating slots; and said cap similar in shape to said bottom seat and having a plurality of ring seats corresponding in location and shape to said plurality of catch seats, per ring seat of said plurality of ring seats said cap further having two ribs and two retaining slots corresponding in location and shape to said two conductive piece locating slots and said two terminal locating slots respectively, said cap joined with said bottom seat such that said plurality of ring seats are joined with said plurality of catch seats, each of said plurality of ring seats provided with a second O-ring capable of holding said piezoelectric crystal in conjunction with said first O-ring.

11. The main structure as defined in claim I further comprising the flow-injection type piezoelectric sensor which in turn comprises:

a cassette having a plurality of openings; and a printed circuit board received inside the cassette, wherein the printed circuit board is provided with a plurality of piezoelectric crystal units which are corresponding in number to said plurality of openings and are separately exposed from said plurality of openings so that the liquid test sample can flow on the piezoelectric crystal units through said plurality of openings;

wherein said printed circuit board has a gold-finger plug-in card at one end thereof, and said gold-finger plug-in card protrudes from said cassette, said gold-finger plug-in card being provided on a surface thereof with a plurality of printed conductive lines, so that the gold-finger plug-in card of the piezoelectric sensor will be electrically in contact with an oscillation circuit of the main structure when the piezoelectric sensor is caught by the retaining slot of the movable stand; and wherein each of said plurality of piezoelectric crystal units comprises a piezoelectric crystal, an upper metal electrode on one side thereof and a lower metal electrode on another side thereof, and said upper and lower metal electrodes are electrically connected to two printed conductive lines of said plurality of printed conductive lines of the gold-finger plug-in card with two printed conductive lines provided on the printed circuit board.

12. The main structure as defined in claim 11, wherein said printed circuit board basically is composed of a surrounding frame and a central panel, said surrounding frame has said gold-finger plug-in card at one end thereof, and said central panel has smooth surfaces and is made of ceramic material, wherein said plurality of piezoelectric crystal units are provided on the central panel and are equidistantly spaced apart with one another.

13. The main structure as defined in claim 12, wherein said cassette is composed of a cap and a bottom seat, said printed circuit board is mounted in the bottom seat, and said cap is fastened to the bottom seat so that the printed circuit board is sealed in the cassette with the gold-finger plug-in card protruding therefrom, wherein said cap has a plurality of holes, and said central panel has a plurality of apertures corresponding to said plurality of holes of said cap, so that said plurality of openings of said cassette are formed when the cap is fastened to the bottom seat, and wherein said plurality of apertures are separately sealed with said plurality of piezoelectric crystal units at the side away from the cap.

14. The main structure as defined in claim 13, wherein said plurality of piezoelectric crystal units are attached to the central panel by using a glue.

15. The main structure as defined in claim 14, wherein said glue is a metallic conductive glue.

* * * * *